US007317142B2

(12) United States Patent
Bootland et al.

(10) Patent No.: US 7,317,142 B2
(45) Date of Patent: Jan. 8, 2008

(54) IMMUNIZATION OF FISH WITH PLANT-EXPRESSED RECOMBINANT PROTEINS

(75) Inventors: Linda Bootland, Crapaud (CA); Katherine Beifuss, Bryan, TX (US)

(73) Assignees: Prodi Gene, Inc., Adel, IA (US); Novartis AG, Basel (CH)

( * ) Notice: Subject to any disclaimer, the term of this patent is extended or adjusted under 35 U.S.C. 154(b) by 201 days.

(21) Appl. No.: 10/733,031

(22) Filed: Dec. 11, 2003

(65) Prior Publication Data

US 2004/0175441 A1 Sep. 9, 2004

Related U.S. Application Data

(60) Provisional application No. 60/433,381, filed on Dec. 13, 2002.

(51) Int. Cl.

*A01H 1/00* (2006.01)
*A61K 39/00* (2006.01)
*C07K 14/415* (2006.01)
*C07K 14/01* (2006.01)
*C07H 21/04* (2006.01)
*C12N 15/34* (2006.01)

(52) U.S. Cl. ................ 800/295; 424/184.1; 424/186.1; 435/235.1; 435/419; 530/350; 536/23.72; 800/278

(58) Field of Classification Search ............. 424/184.1, 424/186.1, 725; 435/235.1, 419; 530/350; 536/23.72; 800/278, 295

See application file for complete search history.

(56) References Cited

U.S. PATENT DOCUMENTS

| | | | | |
|---|---|---|---|---|
| 4,956,282 A * | 9/1990 | Goodman et al. | 435/69.51 |
| 5,654,184 A | 8/1997 | Curtiss et al. | 424/234.1 |
| 5,679,880 A | 10/1997 | Curtiss et al. | 800/298 |
| 5,686,079 A | 11/1997 | Curtiss et al. | 424/234.1 |
| 5,935,570 A * | 8/1999 | Koprowski et al. | 424/93.4 |
| 6,180,614 B1 | 1/2001 | Davis | 514/44 |
| 6,462,027 B2 | 10/2002 | Poet et al. | 514/44 |
| 6,471,964 B1 | 10/2002 | Biering et al. | 424/186.1 |

FOREIGN PATENT DOCUMENTS

| | | |
|---|---|---|
| WO | WO 9404565 | 3/1994 |
| WO | WO 9612801 | 5/1996 |
| WO | WO 9714290 | 4/1997 |
| WO | WO 0238770 | 5/2002 |
| WO | WO 02083072 | 10/2002 |
| WO | 03 017780 | 3/2003 |

OTHER PUBLICATIONS

Pryde et al. "Nucleotide sequence analysis of the serotype-specific epitope of infectios pancreatic necrosis virus" Virology (1993) vol. 129, No. 1-4 pp. 287-293.

Havarstein et al. "Sequence of the large double-stranded RNA segment of the N1 strain of infectious pancreatic necrosis virus: a comparison with other Birnaviridae" J. General Virology (1990) vol. 71, 299-308.

Polk A.E. et al. "Oral delivery in aquaculture: controlled release of proteins from chitosan-alginate microcapsules" Aquacultural Engineering (1994) 13: 311-323.

Wageningen Uni. Dept. of Animal Sciences "Oral vaccination of fish with plant derived protein vaccines" XP-00287469, Cordis, EU Fifth Framework Program Apr. 24, 2003.

Petrie, A.G. "Uptake of recombinant B-subunit of *Escherichia coli* from the hindgut of rainbow trout—applicability as as oral vaccine delivery system." European Association of Fish Pathologists, 11th International Conference "Disease of Fish and Shellfish," Sep. 21-26, 2003, Malta.

Bootland, Linda M. et al. "Oral immunization of Atlantic Salmon with corn-expressed recombinant marker proteins." 3rd International Symposium on fish Vaccinology, Apr. 9-11, 2003, Bergen, Norway (abstract, slides).

Tucker, C. et al. "Assesment of DAN vaccine potential for juvenile Japaneses Flounder *Paralichthys olivaceus*, through the introduction of reporter genes by particle bombardment and histopathology." Vaccine Nov. 22, 2000; 19(7-8):801-9.

Corbeil, S. et al., "Fish DNA vaccine against infectious hematopoietic necrosis virus: efficacy of various routs of immunization" 2000, Fish Shellfish Immunol, Nov. 10(8):711-23.

Corbeil, S. et al. "Evaluation of the protective immunogenicity of the N,P,M,NV and G proteins of infectious hematopoietic necrosis virus in rainbow trout *Oncorhynchus mykiss* using DNA vaccines." Dec. 1999 Dis Aquat Organ, 39(1):29-36.

Nusbaum, KE et al., Protective immunity induced by DNA vaccination of channel catfish with early and late transcripts of the channel catfish herpesvirus (IHV-1) Jan. 15, 2002 Vet Immunol Immunopathol. 84(3-4):151-68.

Clark, TG. Et al., "Developmental expression of surface antigen genes in the parasitis ciliate lchthyophthirius multifillis." Jul. 15, 1992, Proc Natl Acad Sci USA. 89(14):6363-7.

Sato, H. et al. "Expression of YAV proteins and vaccination against viral ascites among cultured juvenile yellowtail" Biosci. Biotechnol. Biochem Jul. 2000: 64(7): 1494-9.

* cited by examiner

*Primary Examiner*—Phuong T Bui
(74) *Attorney, Agent, or Firm*—Patricia A. Sweeney

(57) ABSTRACT

Plants are produced that express an amino acid sequence that, when administered to a fish, produce an antigenic or immune response in the fish. The amino acid sequence in one embodiment is an antigen from an organism that causes pathology in fish. The plant tissue may be fed to the fish, or mixed with other materials and fed to fish, or extracted and administered to the fish.

2 Claims, 15 Drawing Sheets

Figure 1

BAASS:Avidin sequence:

ATGGCCAACAAGCACCTGAGCCTCTCCCTCTTCCTCGTGCTCCTCGGCCTCTCCGCCTCCCT
CGCCAGCGGCGCCAGGAAGTGCTCCCTCACCGGCAAGTGGACCAATGACCTCGGCTCCAACA
TGACCATCGGCGCCGTGAACTCCAGGGGCGAGTTCACCGGCACCTACATCACCGCCGTGACC
GCCACCTCCAACGAGATCAAGGAGTCCCCCCTCCACGGTACCCAGAACACCATCAACAAGAG
GACCCAGCCCACCTTCGGCTTCACCGTGAACTGGAAGTTCTCCGAGTCCACCACCGTGTTCA
CCGGCCAGTGCTTCATCGACCGCAACGGCAAGGAGGTGCTCAAGACCATGTGGCTCCTGAGG
AGCTCCGTGAATGACATCGGCGACGACTGGAAGGCCACCCGCGTGGGCATCAACATCTTCAC
CCGCCTCCGCACCCAGAAGGAGTGA

Figure 3

Maize optimized (mo) *pat* sequence:

atgtcccccgagcgccgccccgtcgagatccgcccggccaccgccgccgacatggccgccgtgtg
cgacatcgtgaaccactacatcgagacctccaccgtgaacttccgcaccgagccgcagaccccgc
aggagtggatcgacgacctggagcgcctccaggaccgctacccgtggctcgtggccgaggtggag
ggcgtggtggccggcatcgcctacgccggcccgtggaaggcccgcaacgcctacgactggaccgt
ggagtccaccgtgtacgtgtcccaccgccaccagcgcctcggcctcggctccaccctctacaccc
acctcctcaagagcatggaggcccagggcttcaagtccgtggtggccgtgatcggcctcccgaac
gacccgtccgtgcgcctccacgaggccctcggctacaccgcccgcggcaccctccgcgccgccgg
ctacaagcacggcggctggcacgacgtcggcttctggcagcgcgacttcgagctgccggccccgc
cgcgcccggtgcgcccggtgacgcagatctga

Figure 5A

LtB Sequence:

gccccgcagtccatcaccgagctctgctccgagtaccacaacacccagatctacaccatcaacga
caagatcctctcctacaccgagagcatggccggcaagcgcgagatggtgatcatcaccttcaagt
ccggcgccaccttccaggtggaggtgccgggctcccagcacatcgactcccagaagaaggccatc
gagcgcatgaaggacaccctccgcatcacctacctcaccgagaccaagatcgacaagctctgcgt
gtggaacaacaagaccccgaactccatcgccgccatcagcatggagaac

Figure 5B

BAASS:LtB sequence:

atggccaacaagcacctgagcctctccctcttcctcgtgctcctcggcctctccgcctccctcgc
cagcggcgccccgcagtccatcaccgagctctgctccgagtaccacaacacccagatctacacca
tcaacgacaagatcctctcctacaccgagagcatggccggcaagcgcgagatggtgatcatcacc
ttcaagtccggcgccaccttccaggtggaggtgccgggctcccagcacatcgactcccagaagaa
ggccatcgagcgcatgaaggacaccctccgcatcacctacctcaccgagaccaagatcgacaagc
tctgcgtgtggaacaacaagaccccgaactccatcgccgccatcagcatggagaact

Figure 6

VP2 sequence from IPNV:

aacaccaacaaggcaaccgcaacttacttgaaatccatcatgcttccagagactggaccagcaag
catcccggacgacataacggagagacacatcctaaaacaagagacctcgtcatacaacctagagg
tctccgaatcaggaagtggcattcttgtttgtttccctggggcaccaggctcacggatcggtgca
cactacagatggaatgcgaaccagacggggctggagttcgaccagtggctggagacgtcgcagga
cctgaagaaagccttcaactacgggaggctgatctcaaggaaatacgacatccaaagctccacac
taccggccggtctctatgctctgaacgggacgctcaacgctgccaccttcgaaggcagtctgtct
gaggtggagagcctgacctacaacagcctgatgtccctaacaacgaacccccaggacaaagtcaa
caaccagctggtgaccaaaggagtcacagtcctgaatctaccaacagggttcgacaaaccatacg
tccgcctagaggacgagacaccccagggtctccagtcaatgaacggggccaagatgaggtgcaca
gctgcaattgcaccgcggaggtacgagatcgacctcccatcccaacgcctacccccccgttcctgc
gacaggaaccctcaccactctctacgagggaaacgccgacatcgtcaactccacaacagtgacgg
gagacataaacttcagtctggcagaacaacccgcaaacgagaccaagttcgacttccagctggac
ttcatgggccttgacaacgacgtcccagttgtcacagtggtcagctccgtgctggccacaaatga
caactacagaggagtctcagccaagatgacccagtccatcccgaccgagaacatcacaaagccga
tcaccagggtcaagctgtcatacaagatcaaccagcagacagcaatcggcaacgtcgccaccctg
ggcacaatgggtccagcatccgtctccttctcatcagggaacggaaatgtccccggcgtgctcag
accaatcacactggtggcctatgagaagatgacaccgctgtccatcctgaccgtagctggagtgt
ccaactacgagctgatcccaaacccagaactcctcaagaacatggtgacacgctatggcaagtac
gacccccgaaggtctcaactatgccaagatgatcctgtcccacagggaagagctggacatcaggac
agtgtggaggacagaggagtacaaggagaggaccagagtcttcaacgaaatcacggacttctcca
gtgacctgcccacgtcaaaggcatggggctggagagacatagtcagaggaattcggaaagtcgca
gctcctgtactgtccacgctgtttccaatggcagcaccactcatcgga

Figure 7

BAASS:VP2 sequence from IPNV:

atggcgaacaagcacctgagccttagcctcttcctcgtgctcctgggcctctccgcctccctcgc
ctccggcaacaccaacaaggcaaccgcaacttacttgaaatccatcatgcttccagagactggac
cagcaagcatcccggacgacataacggagagacacatcctaaaacaagagacctcgtcatacaac
ctagaggtctccgaatcaggaagtggcattcttgtttgtttccctggggcaccaggctcacggat
cggtgcacactacagatggaatgcgaaccagacggggctggagttcgaccagtggctggagacgt
cgcaggacctgaagaaagccttcaactacgggaggctgatctcaaggaaatacgacatccaaagc
tccacactaccggccggtctctatgctctgaacgggacgctcaacgctgccaccttcgaaggcag
tctgtctgaggtggagagcctgacctacaacagcctgatgtccctaacaacgaacccccaggaca
aagtcaacaaccagctggtgaccaaaggagtcacagtcctgaatctaccaacagggttcgacaaa
ccatacgtccgcctagaggacgagacaccccagggtctccagtcaatgaacggggccaagatgag
gtgcacagctgcaattgcaccgcggaggtacgagatcgacctcccatcccaacgcctacccccg
ttcctgcgacaggaaccctcaccactctctacgagggaaacgccgacatcgtcaactccacaaca
gtgacgggagacataaacttcagtctggcagaacaacccgcaaacgagaccaagttcgacttcca
gctggacttcatgggccttgacaacgacgtcccagttgtcacagtggtcagctccgtgctggcca
caaatgacaactacagaggagtctcagccaagatgacccagtccatcccgaccgagaacatcaca
aagccgatcaccagggtcaagctgtcatacaagatcaaccagcagacagcaatcggcaacgtcgc
caccctgggcacaatgggtccagcatccgtctccttctcatcagggaacggaaatgtccccggcg
tgctcagaccaatcacactggtggcctatgagaagatgacaccgctgtccatcctgaccgtagct
ggagtgtccaactacgagctgatcccaaacccagaactcctcaagaacatggtgacacgctatgg
caagtacgaccccgaaggtctcaactatgccaagatgatcctgtcccacagggaagagctggaca
tcaggacagtgtggaggacagaggagtacaaggagaggaccagagtcttcaacgaaatcacggac
ttctccagtgacctgcccacgtcaaaggcatggggctggagagacatagtcagaggaattcggaa
agtcgcagctcctgtactgtccacgctgtttccaatggcagcaccactcatcgga

Figure 8

VP3 sequence from IPNV:

gacgaggagctgcagcgcctcctgaacgccacgatggccagggccaaggaggtccaggacgccga
gatctacaaacttcttaagctcatggcatggaccagaaagaacgacctcaccgaccacatgtacg
agtggtcaaaagaggaccccgatgcactaaagttcggaaagctcatcagcacgccaccaaagcac
cctgagaagcccaaaggaccagaccaacaccacgcccaagaggcgagagccacccgcatatcatt
ggacgccgtgagagccggggcggacttcgccacaccggaatgggtcgcgctgaacaactaccgcg
gcccatctcccgggcagttcaagtactacctgatcactggacgagaaccagaaccaggcgacgag
tacgaggactacataaaacaacccattgtgaaaccgaccgacatgaacaaaatcagacgtctagc
caacagtgtgtacggcctcccacaccaggaaccagcaccagaggagttctacgatgcagttgcag
ctgtattcgcacagaacggaggcagaggtcccgaccaggaccaaatgcaagacctcagggagctc
gcaagacagatgaaacgcaggcccaggaacgccgatgcgccacgcaggaccagggcgccagcgga
accggcaccgcccggacgctcaaggttcacgcccagcggagacaacgctgaggtg

Figure 9

BAASS:VP3 sequence from IPNV:

atggcgaacaagcacctgagccttagcctcttcctcgtgctcctgggcctctccgcctccctcgc
ctccggcgacgaggagctgcagcgcctcctgaacgccacgatggccagggccaaggaggtccagg
acgccgagatctacaaacttcttaagctcatggcatggaccagaaagaacgacctcaccgaccac
atgtacgagtggtcaaaagaggaccccgatgcactaaagttcggaaagctcatcagcacgccacc
aaagcaccctgagaagcccaaaggaccagaccaacaccacgcccaagaggcgagagccacccgca
tatcattggacgccgtgagagccggggcggacttcgccacaccggaatgggtcgcgctgaacaac
taccgcggcccatctcccgggcagttcaagtactacctgatcactggacgagaaccagaaccagg
cgacgagtacgaggactacataaaacaacccattgtgaaaccgaccgacatgaacaaaatcagac
gtctagccaacagtgtgtacggcctcccacaccaggaaccagcaccagaggagttctacgatgca
gttgcagctgtattcgcacagaacggaggcagaggtcccgaccaggaccaaatgcaagacctcag
ggagctcgcaagacagatgaaacgcaggcccaggaacgccgatgcgccacgcaggaccagggcgc
cagcggaaccggcaccgcccggacgctcaaggttcacgcccagcggagacaacgctgaggtg A) Avidin B) LtB (1/80 serum dilution)

IMMUNIZATION OF FISH WITH PLANT-EXPRESSED RECOMBINANT PROTEINS

This application claims priority to U.S. patent application No. 60/433,381 filed on Dec. 13, 2002 and is incorporated by reference in its entirety.

FIELD OF THE INVENTION

This invention relates to the expression of fish disease antigens in transgenic plants and the use of the same as a vaccine.

BACKGROUND OF THE INVENTION

Over the past decade, transgenic plants have been successfully used to express a variety of useful proteins. For example, production of proteases in plants has been achieved (See U.S. Pat. No. 6,087,558); along with production of aprotinin in plants (U.S. Pat. No. 5,824,870); and avidin (U.S. Pat. No 5,767,379). A variety of mammalian bacterial and viral pathogen antigens are included in those proteins that have been successfully produced in plants, such as viral vaccines (U.S. Pat. No. 6,136,320), transmissible gastroenteritis and hepatitis vaccines (U.S. Pat. Nos. 5,914,123 and 6,034,298). These patents, as well as all references cited herein are incorporated herein by reference.

Many of the resulting peptides induced an immunogenic response in mice (Mason et al. (1998) *Vaccine* 16:1336-1343; Wigdorovitz et al. (1999) *Virology* 155:347-353), and humans (Kapusta et al. (1999) *FASEB J.* 13:1796-1799) comparable to that of the original pathogen. After oral delivery, these edible vaccines were immunogenic and could induce protection. Mice fed a basic diet plus corn expressing recombinant *Escherichia coli* heat-labile enterotoxin B-subunit (LtB) mounted a good dose dependent IgG and IgA response (Streatfield et al. "Plant based vaccines—unique advances" *Vaccine* (2001)19:2742-2748.) Some of the first edible vaccine technologies developed include transgenic potatoes expressing hepatitis, TGEV and Norwalk virus antigens as well as various other viral antigens. (See, e.g., Thanavala et al. (1995) *Proc. Natl. Acad. Sci. U.S.A.* 92:3358-3361; U.S. Pat. No. 6,136,320; U.S. Pat. No. 6,034,298; U.S. Pat. No. 5,914,123; U.S. Pat. No. 5,612,487 and U.S. Pat. No. 5,484,719; Mason et al., (1996) *Proc. Natl. Acad. Sci.* 93:5335-5340; "VP1 protein for foot-and-mouth disease" (Wigdorovitz et al (1999) *Virology* 255:347-353).

The utilization of transgenic plants for vaccine production has several potential benefits over traditional vaccine production methods. First, transgenic plants are usually constructed to express only a small antigenic portion of the pathogen or toxin, eliminating the possibility of infection or innate toxicity of the whole organism and reducing the potential for adverse reactions. Second, since there are no known human or animal pathogens that are able to infect plants, concerns with viral or prion contamination are eliminated. Third, immunogen production in transgenic crops relies on the same established technologies to sow, harvest, store, transport, and process the plant as those commonly used for food crops, making transgenic plants a very economical means of large-scale vaccine production. Fourth, expression of immunogens in the natural protein-storage compartments of plants maximizes stability, minimizes the need for refrigeration and keeps transportation and storage costs low. Fifth, formulation of multicomponent vaccines is possible by blending the seed of multiple transgenic plant lines into a single vaccine. Sixth, direct oral administration is possible when immunogens are expressed in commonly consumed food plants, such as grain, leading to the production of edible vaccines.

Oral vaccine delivery as the primary or booster immunization is by far the most sought after method by the aquaculture industry because it is suitable for the mass immunization of fish of all sizes, it is less stressful on fish than injection delivery, which requires handling of the fish, and because it induces mucosal immunity. However the cost-effectiveness of oral delivery has been a major barrier to commercialization of this method, especially for larger fish. Efficacy of oral antigen delivery is reported to be limited by the destruction and absorption of the antigens by the fish digestive system.

The inventors have found that transgenic plants can provide an ideal system for economical production of antigens for oral vaccination of fish.

BRIEF DESCRIPTION OF THE INVENTION

According to one aspect of the invention there is provided use of a plant-derived recombinant amino acid sequence in the manufacture of a medicament for the prevention or treatment of disease in fish, wherein the amino acid sequence, when administered to fish, produces an antigenic or immunogenic response in the fish. Preferably the recombinant amino acid sequence is an antigen of an organism that causes disease or pathology in fish.

In one aspect of the invention a plant is transformed with a nucleotide sequence encoding an amino acid sequence which, when administered to a fish, produces an antigenic or immunogenic response in the fish.

In a further aspect of the invention, expression of the amino acid sequence is preferentially directed to the seed of the plant.

In another aspect, the invention provides an amino acid sequence derived by expression in a plant cell, wherein said amino acid sequence is endogenous to an organism causing disease or pathology in fish.

In another aspect, the invention provides a composition suitable for oral delivery to fish, comprising a plant-derived recombinant amino acid sequence, in particular a plant-derived recombinant amino acid sequence which is an antigen of an organism that causes disease or pathology in a fish.

In yet another aspect, the invention provides a method of immunizing fish against disease, which comprises administering to a fish a composition comprising a plant-derived recombinant amino acid sequence which is an antigen of an organism that causes disease or pathology in a fish.

BRIEF DESCRIPTION OF THE FIGURES

FIG. 1 shows the barley alpha amylase sequence fused to a sequence encoding the avidin mature protein (SEQ ID NO: 1).

FIG. 3 shows the maize optimized pat sequence (SEQ ID NO: 2).

FIG. 5A is the nucleotide sequence of maize codon optimized LtB (SEQ ID NO: 3).

FIG. 5B is the nucleotide sequence of BAASS:LtB (SEQ ID NO: 4).

FIG. 6 is the nucleotide sequence of IPNV VP2 (SEQ ID NO: 5).

FIG. 7 is the nucleotide sequence of BAASS:VP2 (SEQ ID NO: 6).

FIG. 8 is the nucleotide sequence of IPNV VP3 (SEQ ID NO: 7).

FIG. 9 is the nucleotide sequence of BAASS:VP3 (SEQ ID NO: 8).

DETAILED DESCRIPTION OF THE PREFERRED EMBODIMENT

Figure 2:
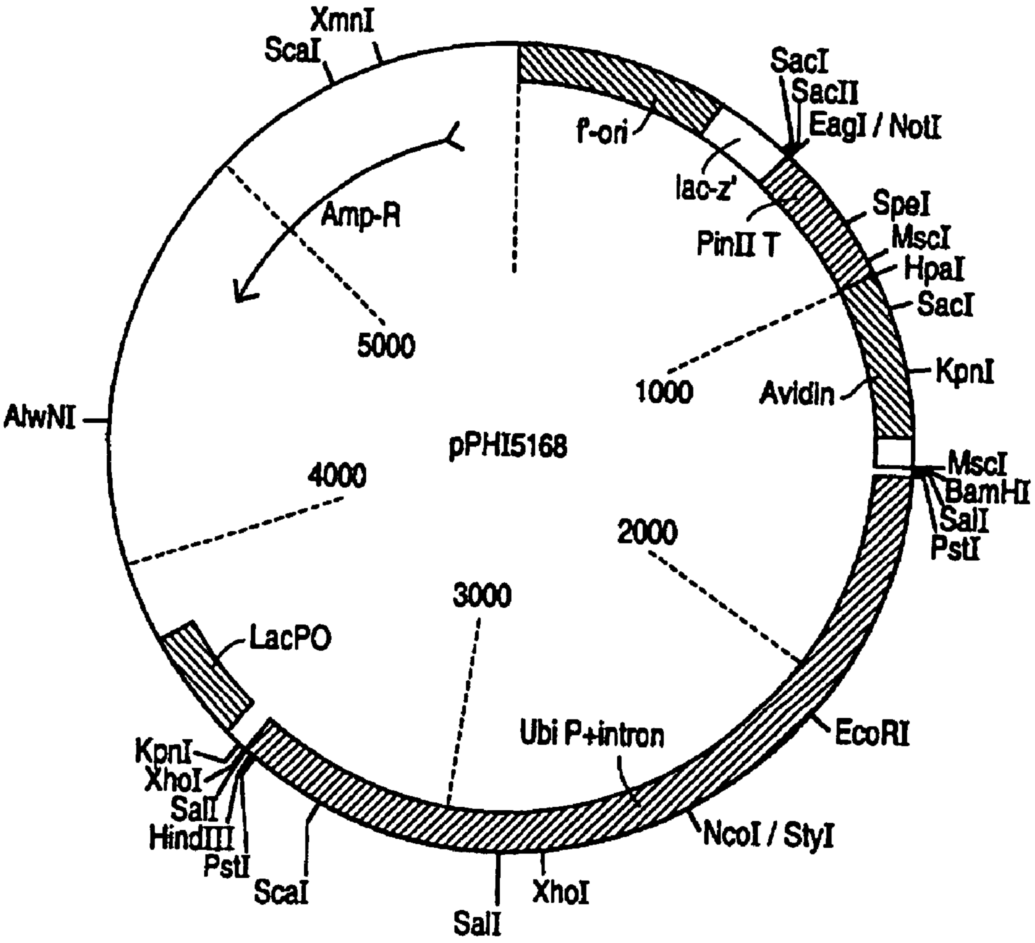
FIG. 2 is a plasmid map of pPHI5158.

By use of the term "fish" herein is meant fin-fish, shellfish, and other aquatic animals. Fin-fish include all vertebrate fish, which may be bony or cartilaginous fish. The prime candidate fin-fish species for receiving the vaccine of the invention are salmonid fish, including salmon and trout species, particularly coho salmon (*Oncorhynchus kisutch*), brook trout (*Salvelinus fontinalis*), brown trout (*Salmo trutta*), chinook salmon (*Oncorhynchus tshawytscha*), masu salmon (*Oncorhynchus masou*), pink salmon (*Oncorhynchus gorbuscha*), rainbow trout (*Oncorhynchus mykiss*), Arctic charr (*Salvelinus alpinus*) and Atlantic salmon (*Salmo salar*). However, any other fish species susceptible to infectious disease may benefit, such as ornamental fish species, koi, goldfish, carp, catfish, yellowtail, sea bream, sea bass, pike, halibut, haddock, tilapia, turbot, wolffish, and so on.

Examples of shellfish include, but are not limited to clams, lobster, shrimp, crab and oysters. Other cultured aquatic animals include, but are not limited to eels, squid and octopi.

A "plant-derived" recombinant amino acid sequence is an amino acid sequence engineered to be expressed in a transgenic plant whose sequence is not endogenous to the plant.

An amino acid sequence of the invention is one which, when administered to a fish, results in an antigenic or immunogenic response in the fish.

Antigens of organisms causing pathologies in fish and nucleotide sequences encoding such antigens have been administered to fish that have been exposed by way of injection, immersion, spray, adding the vaccine directly to fish food, or gene transfer into fish cells. For example, U.S. Pat. No. 6,462,027 describes a method of contacting an isolated non-infectious polynucleotide encoding an immunogen with an aquatic animal. U.S. Pat. No. 6,180,614 describes introducing DNA plasmids encoding antigen-based vaccines by transfection into the fish. The promoter is one capable of directing expression in the fish. The patent specification notes that bacterially-expressed recombinant proteins can form inclusion bodies so that recovery of protein is low or nonexistent. Further, it indicates induction of an immune response may require that the antigenic protein be correctly glycosylated and folded, which, they state, may not be accomplished in a cell other than an animal cell. However, the inventors here have found that it is possible to produce in a plant a correctly processed antigenic amino acid sequence that can cause an antigenic or immunogenic response when administered to fish.

The coding sequences of many amino acid sequences producing an antigenic or immunogenic response in fish (also referred to as an "antigen") have been and are being sequenced, as there has been a great interest in producing vaccines using such genes. While specific examples are set forth below to illustrate the principle of the invention using certain antigens, the invention is not limited to any particular antigen. Rather any amino acid sequence that produces an antigenic or immune response in a fish can be used. In a preferred embodiment, an antigen of an organism causing pathologies in fish is used. Such an antigen is used to induce or enhance immunity, and the corresponding nucleotide sequence which encodes that antigen is useful in the invention. A few of the numerous example of such sequences which have been isolated include the cDNA encoding structural protein-1 of infectious salmon anemia virus (ISAV) described in U.S. Pat. No. 6,471,964, as well as those discussed in Tucker et al. (2000) "Assessment of DNA vaccine potential for juvenile Japanese flounder *Paralichthys olivaceus*, through the introduction of reporter genes by particle bombardment and histopathology" *Vaccine* 19(7-8): 801-809; Corbeil et al. (1999) "Evaluation of the protective immunogenicity of the N, P, M, NV, G proteins of infectious hematopoietic necrosis virus in rainbow trout *Oncorhynchus mykiss* using DNA vaccines" *Dis. Aquat. Organ* 39(1):29-26; Nusbaum et al. (2002) "Protective immunity induced by DNA vaccination of channel catfish with early and late transcripts of the channel catfish herpes virus (IHV-1)" *Vet Immunol. Immunopathol* 84(3-4):151-168; Clark et al. (1992) "Developmental expression of surface antigen genes in the parasitic cilate *Ichtyophthirius multifiliis*" *Proc. Natl. Acad. Sci.* 89(14):6363-6367; and Sato et al. (2000) "Expression of YAV proteins and vaccination against viral ascites among cultured juvenile yellowtail" *Biosci. Biotechnol. Biochem.* 64(7):1494-1497.

Examples of the variety of pathogens for which the methods of the invention can be useful include, without limitation, hemorrhagic septicemia virus (VHSV), infectious pancreatic necrosis virus (IPNV), infectious haematopoietic necrosis virus (IHNV), salmon pancreas disease virus (SPDV), virus causing spring viremia of carp, grass carp hemorrhagic virus, nodaviridae such as nervous necrosis virus or striped jack nervous necrosis virus, infectious salmon anaemia virus (ISAV), *Aeromonis salmonicida, Renibacterium salmoninarum*, Yersinia spp., Pasteurella spp. (including *Photobacterium damselae*), Vibrio spp. (including *V. anguillarum* and *V. ordalii*), Edwardsiella spp. (including *E. ictaluri* and *E. tarda*), *Piscirickettsia salmonis* (causative of Salmonid Rickettsial Septicaemia), Iridovirus, cardiomyopathy syndrome virus, taura syndrome virus, Penaeus monodon virus, shrimp yellowhead virus, shrimp whitespot virus, and Streptococci spp.

Other examples of known antigens that produce pathology in fish that can be used in the invention include: IPNV VP2 and VP3 proteins, IHNV G protein, VHSV G protein, Nodavirus capsid protein, ISAV antigens disclosed in WO 01/10469, SPDV antigens disclosed in WO 99/58639, *P. salmonis* antigens disclosed in WO 01/68865, and Whitespot Virus antigens disclosed in WO 01/09340. Numerous nucleic acid and amino acid sequences of fish pathogen antigens are known and accessible through the Genbank databases and other sources.

An amino acid sequence or antigen of the invention which is "of an organism causing disease or pathology in fish" is an amino acid sequence or antigen of a pathogen of fish (or a derivative thereof), which is expressed in plant cells through recombinant DNA technology, as described below. The "antigens" used in practicing the invention may be full-length antigenic proteins from a virus, bacterium, fungus, parasite, protozoan, etc., that causes disease in fish, or alternatively may constitute an immunogenic portion, fragment or derivative of same. A "derivative" of an amino acid sequence is a sequence related to the reference sequence either on the amino acid sequence level or at the 3D level (i.e. molecules having approximately the same shape and configuration as the reference sequence). Derivatives include sequence homologues, mutants, mimetics, mimotopes, analogues, monomeric forms and functional equivalents whether obtained directly from the organism or synthetically produced, which are capable of inducing an antigenic or immunogenic response in fish. Particular mention may be made of derivatives resulting from amino acid substitutions (with natural or synthetic amino acids), deletions, inversions, insertions, and additions.

This antigen, whether it is an amino acid sequence or protein, is the "antigen of interest". The "gene of interest" refers to the nucleotide sequence that encodes for the polypeptide or protein that is the desired antigen or selection marker. The gene of interest can be optimized for plant transcription and translation by optimizing the codons used for plants (see discussion below).

In general, the methods available for construction of recombinant genes described above, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning. The methods involved are standard methods for a molecular biologist Sambrook et al., *Molecular Cloning A Laboratory Manual*, Cold Spring Harbor Laboratory Press, Second Edition (1989).

Once the gene is engineered to contain desired features, such as the desired localization sequences, it is placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence, which in this context would code for the antigen of interest; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker that is functionally linked to a promoter that controls transcription initiation. By "functionally linked" it is understood that the gene of interest (in this case the gene encoding a selection marker) is down-stream of the promoter in the correct orientation and in the correct frame alignment such that transcription of mRNA and translation of the mRNA occurs correctly to produce the desired polypeptide or protein. For a general description of plant expression vectors and reporter genes, see Gruber et al. (1993) "Vectors for Plant Transformation" in *Methods of Plant Molecular Biology and Biotechnology* CRC Press. p 89-119. In one embodiment, the selective gene is a glufosinate-resistance encoding DNA and in another embodiment can be the phosphinothricin acetyl transferase ("pat") or maize optimized pat gene under the control of the CaMV 35S promoter. The gene confers resistance to bialaphos (Gordon-Kamm (1990) *The Plant Cell* 2: 603; Uchimiya et al. (1993) *Bio/Technology* 11: 835; and Anzai et al. (1989) *Mol. Gen. Gen.* 219: 492).

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Although the endogenous promoter of a structural gene of interest may be utilized for transcriptional regulation of the gene, the promoter is often a foreign regulatory sequence. Promoter elements employed to control expression of antigenic proteins and the selection gene, respectively, can be any plant-compatible promoter. Those can be plant gene promoters, such as, for example, the ubiquitin promoter (European patent application no. 0 342 926); the promoter for the small subunit of ribulose-1,5-bis-phosphate carboxylase (ssRUBISCO) (Coruzzi, et al., *EMBO J.,* 3:1671, 1984; Broglie, et al., *Science,* 224:838, 1984); or promoters from the tumor-inducing plasmids from *Agrobacterium tumefaciens*, such as the nopaline synthase and octopine synthase promoters (carried on tumor-inducing plasmids of *Agrobacterium tumefaciens* and have plant activity); or viral promoters such as the cauliflower mosaic virus (CaMV) 19S and 35S promoters of CaMV (Brisson, et al., *Nature,* 310:511, 1984; Odell, et al., Nature, 313:810, 1985), the figwort mosaic virus 35S promoter(Gowda, et al., *J. Cell Biochem.,* 13D: 301, 1989) or the coat protein promoter of TMV (Takamatsu, et al., *EMBO J.* 6:307, 1987. See also Kay et al. (1987) "Duplication of CaMV 35S promoter sequences creates a strong enhancer for plant genes" *Science* 236:199-1302 and European Patent Application EP-A-342 926. Alternatively, plant promoters such as the mannopine synthase promoter (Velten, et al., *EMBO J.,* 3:2723, 1984); heat shock promoters, e.g., soybean hspl7.5-E or hspl 7.3-B (Gurley, et al., *Mol. Cell. Biol.,* 6:559, 1986; Severin, et al., *Plant Mol. Biol.,* 15:827, 1990); or ethanol-inducible promoters (Caddick et al., *Nature Biotech.,* 16:177, 1998) may be used. See International Patent Application No. WO 91/19806 for a review of illustrative plant promoters suitably employed in the present invention. In one embodiment of the present invention, the amino acid-encoding DNA is under the transcriptional control of PGNpr6 promoter (WO 01/94394). This is a ubiquitin-like promoter.

In a preferred embodiment, a tissue specific promoter is provided to direct transcription of the DNA preferentially to the seed. One such promoter is the globulin promoter. This is the promoter of the maize globulin-1 gene, described by Belanger, F. C. and Kriz, A. L. (1991) "Molecular basis for allelic polymorphism of the maize globulin-1 gene" *Genetics* 129: 863-972. It also can be found as accession number L22344 in the Genbank database. Another example is the phaseolin promoter. See, Bustos et al. (1989) "Regulation of B-glucuronidase expression in transgenic tobacco plants by an A/T-rich cis-acting sequence found upstream of a french bean B-phaseolin gene", *The Plant Cell* (1): 839-853.

The expression vector can optionally also contain a signal sequence located between the promoter and the gene of interest. A signal sequence is a nucleotide sequence, and possibly the corresponding amino acid sequence, which is used by a cell to direct the protein or polypeptide of interest to be translated and placed in a particular place within or outside the eukaryotic cell. One example of a plant signal sequence is the barley α-amylase secretion signal (Rogers, (1985) *J. Biol Chem* 260, 3731-3738). Many signal sequences are known in the art. See, for example Becker et al. (1992), *Plant Mol. Biol.* 20:49; Close, P. S., (1993) Master's Thesis, Iowa State University; Knox, C. (1987), et al., "Structure and Organization of Two Divergent Alpha-Amylase Genes from Barley", *Plant Mol. Biol.* 9:3-17; Lerner et al., (1989) *Plant Physiol.* 91:124-129; Fontes et al. (1991), *Plant Cell* 3:483-496; Matsuoka et al. (1991), *Proc. Natl. Acad. Sci.* 88:834; Gould et al. (1989), *J. Cell. Biol.* 108:1657; Creissen et al. (1991), *Plant J.* 2:129; Kalderon, et al. (1984) "A short amino acid sequence able to specify nuclear location" *Cell* 39:499-509; and Steifel, et al. (1990) "Expression of a maize cell wall hydroxyproline-rich glycoprotein gene in early leaf and root vascular differentiation" *Plant Cell* 2:785-793.

In one embodiment, the plant selection marker and the gene of interest can be both functionally linked to the same promoter. In another embodiment, the plant selection marker and the gene of interest can be functionally linked to different promoters. In yet a third and fourth embodiments, the expression vector can contain two or more genes of interest that can be linked to the same promoter or different promoters.

Obviously, many variations on the promoters, selectable markers, signal sequences and other components of the construct are available to one skilled in the art.

In accordance with the present invention, a transgenic plant is produced that contains a DNA molecule, comprised of elements as described above, integrated into its genome so that the plant can express the gene of interest and thus produce the antigen of interest. The transgenic plant may suitably be a species that is conventionally cultivated for animal feed, such as corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), potato (*Solanum tuberosum*), tomatoes (*Lycopersicon esculentum*), and peas (Lathyrus spp.). Alternatively, the transgenic plant may be a species that is not conventionally eaten, such as tobacco (*Nicotiana tabacum*), cotton (*Gossypium hirsutum*), tea (*Camellia sinensis*), flax (Linum), sisal (Agave spp., Furcraea spp.), pines, firs and cedars. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al. (1993) "Procedures for Introducing Foreign DNA into Plants" in *Methods in Plant Molecular Biology and Biotechnology*, Glick et al (eds) CRC Press pp. 67-68 and by Phillips et al. (1988) "Cell/Tissue Culture and In Vitro Manipulation" in *Corn and Corn Improvement* 3d Edit. Sprague et al (eds) American Soc. of Agronomy pp. 345-387. The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al. (1992) *Bio/Technology* 10:26; and Weisinger et al. (1988) *Ann. Rev. Genet.* 22: 421-477. For example, the DNA construct may be introduced into the genomic DNA of the plant cell using techniques such as microprojectile-mediated delivery (Klein et al. (1987) *Nature* 327: 70-73); electroporation (Fromm et al. (1985) *Proc. Natl. Acad. Sci.* 82: 5824); polyethylene glycol (PEG) precipitation (Paszkowski et al. (1984) *Embo. J.* 3: 2717-272); direct gene transfer (WO 85/01856 and EP-A-275 069); in vitro protoplast transformation (U.S. Pat. No. 4,684,611) and microinjection of plant cell protoplasts or embryogenic callus (Crossway, (1985) *Mol. Gen. Genetics* 202:179-185). Cocultivation of plant tissue with *Agrobacterium tumefaciens* is another option, where the DNA constructs are placed into a binary vector system (Ishida et al. (1996) "High efficiency transformation of maize (*Zea mays* L.) mediated by *Agrobacterium tumefaciens" Nature Biotechnology* 14:745-750). The virulence functions of the *Agrobacterium tumefaciens* host will direct the insertion of the construct into the plant cell DNA when the cell is infected by the bacteria. See, for example Horsch et al. (1984) *Science* 233: 496-498, and Fraley et al. (1983) *Proc. Natl. Acad. Sci.* 80: 4803.

Standard methods for transformation of canola are described by Moloney et al. (1989) "High Efficiency Transformation of *Brassica napus* Using *Agrobacterium* Vectors" *Plant Cell Reports* 8:238-242. Corn transformation is described by Fromm et al. (1990) *Bio/Technology* 8:833 and Gordon-Kamm et al, supra. *Agrobacterium* is primarily used in dicots, but certain monocots such as maize can be transformed by Agrobacterium. See for example, U.S. Pat. No. 5,550,318. Rice transformation is described by Hiei et al. (1994) "Efficient transformation of rice (*Oryza sativs* L.) mediated by *Agrobacterium* and sequence analysis of the boundaries of the T-DNA" *The Plant Journal* 6(2): 271-282, Christou et al. (1992) *Trends in Biotechnology* 10:239 and Lee et al. (1991) *Proc. Nat. Acad. Sci. USA* 88:6389. Wheat can be transformed by techniques similar to those used for transforming corn or rice. Sorghum transformation is described by Casas et al. (1997) "Transgenic sorghum plants obtained after microprojectile bombardment of immature inflorescences" *In vitro cellular and developmental biology, Plant.* 33:92-100 and by Wan et al. (1994) *Plant Physiology.* 104:37. Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi II maize line is used which initiates Type II embryogenic callus in culture. While Ishida recommends selection on phosphinothricin when using the bar or pat gene for selection, another preferred embodiment provides for use of bialaphos instead. In general, as set forth in the '616 patent, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue and suspension cells, for example. In this preferred embodiment, the suspension of Agrobacterium has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid. EHA101 contains a disarmed pTi that carries resistance to kanamycin. Hood E E, Helmer G L, Fraley R T, Chilton M D (1986) “The hypervirulence of *Agrobacterium tumefaciens* A281 is encoded in a region of pTiBo542 outside of T-DNA” *J. Bacteriol* 168: 1291-1301.

Further, the Ishida protocol as described provides for growing fresh culture of the Agrobacterium on plates, scraping the bacteria from the plates, and resuspending in the co-culture medium as stated in the ’616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 , preferably between 0.2 and 0.5. The bacteria are then centrifuged to remove the media and resuspended in the co-culture medium. Since Hi II is used, medium preferred for Hi II is used. This medium is described in considerable detail by Armstrong, C. I. and Green C. E. (1985) “Establishment and maintenance of friable, embryogenic maize callus and involvement of L-proline” *Planta* 154:207-214. The resuspension medium is the same as that described above. All further Hi II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes “reprogrammed” to have a new identity. Thus the scutellum cells become embryogenic callus.

It is preferred to select the highest level of expression of the amino acid sequence, and it is thus useful to ascertain expression levels in transformed plant cells, transgenic plants and tissue specific expression. One such method is to measure the expression of the antigen of interest as a percentage of total soluble protein. One standard assay is the Bradford assay which is well known to those skilled in the art (Bradford, M. (1976) *Anal. Biochem.* 72:248). The biochemical activity of the recombinant amino acid sequence should also be measured and compared with a wild-type standard.

The levels of expression of the gene of interest can be enhanced by the stable maintenance of the gene of interest on a chromosome of the transgenic plant. Use of linked genes, with herbicide resistance in physical proximity to the gene of interest, would allow for maintaining selective pressure on the transgenic plant population and for those plants where the genes of interest are not lost.

With transgenic plants according to the present invention, the amino acid sequence can be produced in commercial quantities. Thus, the selection and propagation techniques described above yield a plurality of transgenic plants that are harvested in a conventional manner. The plant seed expressing the recombinant amino acid sequence can be used in a commercial process, or the amino acid sequence can be extracted. When using the seed itself, it can, for example, be made into flour and then applied in the commercial process. Extraction from biomass can be accomplished by known methods. Downstream processing for any production system refers to all unit operations after product synthesis, in this case protein production in transgenic seed (Kusnadi et al. (1997) *Biotechnology and bioengineering.* 56:473-484). Seed is processed either as whole seed ground into flour, or fractionated, and the germ separated from the hulls and endosperm. If germ is used, it is usually defatted using a hexane extraction and the remaining crushed germ ground into a meal or flour. In some cases the germ is used directly or the amino acid sequence can be extracted (See, e.g. WO 98/39461). Extraction is generally made into aqueous buffers at specific pH to enhance recombinant amino acid sequence extraction and minimize native seed protein extraction. Subsequent amino acid sequence concentration or purification can follow.

In a further embodiment, plant breeding can be used to introduce the gene into other plants once transformation has occurred. This can be accomplished by any means known in the art for breeding plants such as, for example, cross pollination of the transgenic plants that are described above with another plant, and selection for plants from subsequent generations which express the amino acid sequence. The plant breeding methods used herein are well known to one skilled in the art. For a discussion of plant breeding techniques, see Poehlman (1987) *Breeding Field Crops*, AVI Publication Co., Westport Conn. Many crop plants useful in this method are bred through techniques that take advantage of the plant’s method of pollination. A plant is self-pollinating if pollen from one flower is transferred to the same or another flower of the same plant. A plant is cross-pollinated if the pollen comes from a flower on a different plant. For example, in Brassica, the plant is normally self sterile and can only be cross-pollinated unless, through discovery of a mutant or through genetic intervention, self compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described at Brar et al., U.S. Pat. Nos. 4,654,465 and 4,727,219 and Albertsen et al. U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as *Plant Breeding Methodology* edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

The preferred method of administration of plant-derived recombinant amino acid sequence to fish is per oral, optionally by admixture of the recombinant amino acid sequence to a conventional feedstuff. Alternative methods of administration include immersion, intra-peritoneal injection, and intramuscular injection.

Transgenic plant tissue may be fed to the fish, or mixed with other materials and fed to fish, or extracted and administered to the fish.

Oral delivery forms of the vaccine encompass any combination of the recombinant amino acid sequence with one or more excipients and optionally with one or more nutrients. Excipients as used herein can include silica, binding agents, emulsions, tensio-active substances, fatty acids, fats, oils etc. and any other additives necessary for preparing the composition.

Typical fish feedstuffs can comprise various nutrient sources, such as a metabolizable energy source (carbohydrate), a protein source, a fat source, and optionally fibers, vitamins and minerals. The exact composition of the feedstuff depends on the type of fish concerned, and in particular whether or not the fish are carnivorous. On a commercial scale feedstuffs may conveniently be provided in the form of pressed or extruded feed pellets. Plant-derived recombinant amino acid sequence may be incorporated into the feed by substitution for a more usual protein source (such as fish meal, blood meal, maize gluten, soya meal etc.). Alternatively, the plant-derived recombinant amino acid sequence may be adhered to the surface of a pre-formed fish feedstuff.

The plant-derived recombinant amino acid sequence may be enteric-coated for oral delivery. The enteric coating protects the vaccine from proteases and from the relatively low pH levels of the stomach. This allows the vaccine to reach the hindgut associated with lymphoid tissue, which maximizes the effectiveness of the vaccine for protecting fish. The enteric coating typically comprises a polymer coating that is unaffected by acidic pH, but which is dissolved upon passing to the higher pH environments of the intestine.

In a preferred embodiment the plant-derived recombinant amino acid sequence is administered to fish in the form of transgenic plant material, such as plant seeds, leaves, fruits, stems, tubers, etc., preferably where the transgenic plant material is not admixed to any other feedstuffs. In another embodiment the plant-derived recombinant amino acid sequence is physically (reversibly) mixed with pre-formed fish feed immediately prior to feeding the fish.

In order to avoid unnecessary extraction procedures, it is preferred to deliver the plant-derived recombinant amino acid sequence in a non-purified (crude) form to the fish. This means that edible parts of the source plant are not specially treated or processed in order to extract or concentrate the recombinant amino acid sequence.

The effective dosage of vaccine may vary depending on the size and species of the subject, and according to the mode of administration. The optimal dosage can be determined through trial and error by a veterinarian or aquaculture specialist. Vaccines may comprise between about 1 and 1000 μg, preferably between about 10 and 200 μg, more preferably between about 50 and 100 μg of recombinant amino acid sequence in a single dosage.

The vaccine of the invention may be administered to fish for prophylactic or therapeutic purposes. The vaccine is capable of inducing long term protection against the target infectious disease. "Long term" protection in the case of fish means a protective immune response for longer than 7 days, more preferably longer than 20 days, and most preferably longer than 70 days post vaccination.

EXAMPLE 1

Transformation of Avidin into Plants and Detection of Expression Levels

Construction of Plasmids for Avidin Expression in Plants

Construction of plasmids for avidin transformation into corn is described in U.S. Pat. No. 5,767,379, incorporated herein by reference. The chicken egg white avidin cDNA was reported by Gope M L. (1987), et al., *Nuc. Acids Res.* 15: 3595-3606. The amino acid sequence is reverse translated into nucleic acid sequence utilizing a preferred maize codon usage table (GCG, assembled by Mike Cherry, Stanford University). From this computer-generated synthetic sequence, overlapping, complementary oligonucleotides with compatible restriction site termini are designed, then annealed and ligated to yield the maize optimized gene. The sequence used is set forth in the '379 patent, incorporated by reference. The barley alpha amylase signal sequence ((Rogers, (1985) *J. Biol Chem* 260, 3731-3738) is also synthesized (using overlapping, complementary nucleotides) with maize-preferred codons. Compatible restriction sites between these two gene fragments are ligated, with the barley alpha amylase signal sequence at the 5' end of the avidin gene and in proper frame alignment so that the correct codon usage occurs during translation to yield the desired antigen. The resultant barley alpha amylase signal sequence/avidin segment is cloned, (See FIG. 1 (SEQ ID NO: 1)) as a BamHI/EcoRI fragment, into the vector pGEM3Zf+, a product of Promega Corporation (Madison, Wis.), to generate plasmid pPHI5142. A BamHI/HpaI fragment containing the barley alpha amylase signal sequence/avidin region is isolated and cloned into a plasmid derived from pBlueScript SK+ (Stratagene, La Jolla, Calif.), as a backbone. In this plasmid, the signal sequence/avidin gene fragment is inserted, in the correct orientation, between the maize ubiquitin 5' region, which includes the maize ubiquitin promoter (UBI1ZM), the first exon and first intron, and the potato proteinase inhibitor II (PinII) transcription terminator region (An et al, (January 1989 (*Plant Cell* 1:115-122). The resultant plasmid is pPHI5168 (FIG. 2). Co-transformed with the plasmid is a plasmid (pPHI610) containing the bar gene from *Streptomyces hygroscopicus*, supra and White J. (1990) *Nucleic Acids Res* 18:1062 linked to the double 35S promoter (e.g. Friz, S. E. *J. Cell Sci* 98:545-550), the intron from the maize alcohol dehydrogenase gene (Callis J., et al. *Genes and Development* 1:1183-1200) and the PinII terminator (An G., et al. (1989) *Plant Cell* 1:115-122). These constructs and the process used are fully described in the '379 patent, supra. Note that in the experiment described in the '379 patent, the bar gene is used, where in the other experiments described herein the maize optimized pat gene is used. FIG. 3 sets forth this sequence (SEQ ID NO: 2).

Transformation and Tissue Culture to Produce Avidin-Expressing Plants.

An established callus line derived from a single immature embryo of the "Hi II" maize plants (Armstrong C L, Green C E, Phillips R L (1991) *Maize Gen. Coop. Newsletter,* 65:92-93) is transformed using particle bombardment-mediated transformation with a helium-powered particle acceleration device, PDS 1000 (Bio-Rad, Hercules, Calif.). Hi II is a corn plant line used in research frequently because of its ease in transformation. Tissue showing a friable type-II embryogenic morphology is sieved through 710 m mesh prior to co-transformation with equimolar amounts of the avidin gene (pPHI5168) and the bar selectable marker gene (PHP610), according to the procedures of Tomes et al. (Tomes D T, Ross M C, Songstad D D (1995) *Plant Cell Tissue and Organ Culture: Fundamental Methods*. Springer-Verlag, Berlin, Heidelberg. pp.197-213). Transformants expressing the bar gene are selected in the presence of bialaphos (3 mg $l^{-1}$), according to the protocol of Register et al. (Register J. C.-III et al. (1994), *Plant Mol. Biol.* 25:951-961). Co-transformants that also express the avidin gene are identified by ELISA screening of the selected colonies. Multiple plants ($T_0$ generation) are regenerated from avidin-expressing colonies, transferred to the greenhouse and assayed for avidin expression in leaf tissue.) $T_1$ seed is obtained by outcrossing, with the $T_0$ plants as the female parent and a non-transformed inbred line (PHN46; see U.S. Pat. No. 5,567,861) as the male parent.

ELISA to Detect Avidin in Corn.

The following procedures are used to detect expression of avidin in seeds. Seeds are powdered and extracted in 10 mM PBS pH 7.0 containing 0.05% Tween-20 (PBST). Total protein was quantified using the Bradford microtiter assay Bradford (Bradford, M. M. 1976. A rapid and sensitive method for the quantitation of microgram quantities of protein utilizing the principal of protein-dye binding. *Anal. Biochem.* 72:248-254). ELISAs are typical sandwich style in which the microtiter plates are coated with rabbit anti-avidin antibody, the avidin protein is captured overnight at 4° C., and the plate is reacted with goat anti-avidin antibody (Vector Labs, Burlingame, Calif.) followed by anti-goat alkaline phosphatase conjugate (Jackson Immunoresearch, West Grove, Pa.). The alkaline phosphatase is detected with para-nitrophenyl phosphate and read at 405 nm on a SpectroMax plate reader (Molecular Devices, Sunnyvale, Calif.).

EXAMPLE 2

Transformation of LtB into Plants and Detection of Expression

Figure 4:
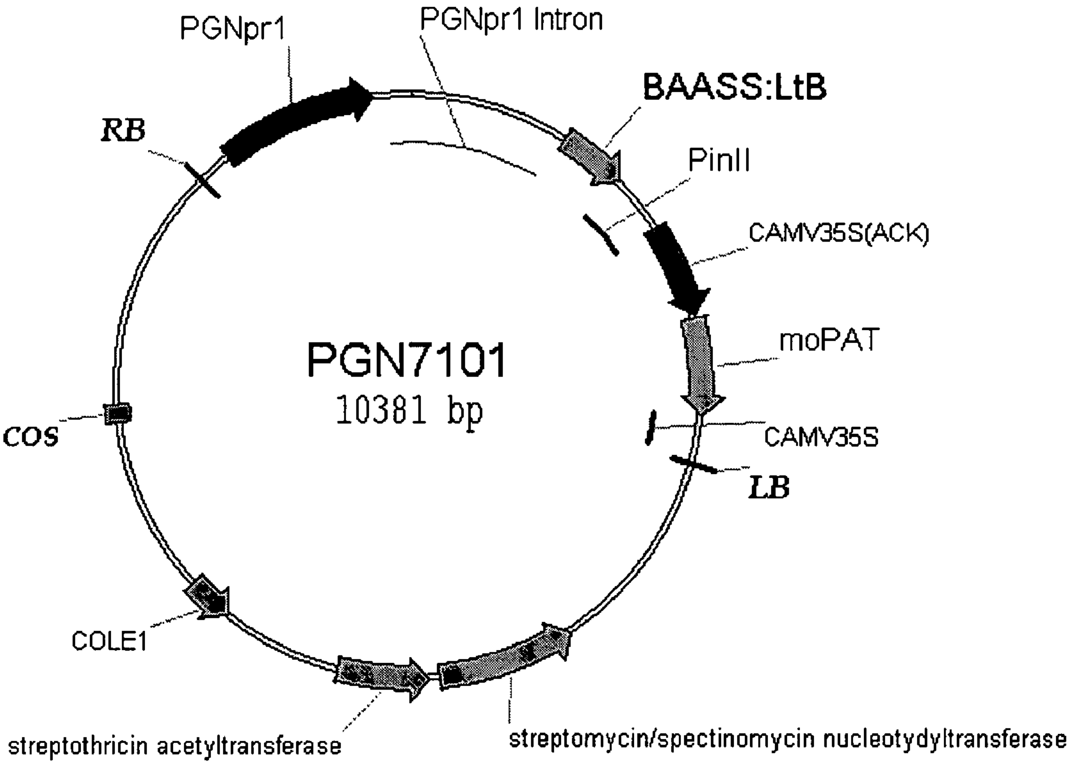
FIG. 4 is a plasmid map of PGN7101.

LtB sequences and introduction into plants is described at U.S. Pat. No. 6,194,560, which sequences and methods were used in this experiment, and which is incorporated herein by reference. The vector used here differs in certain aspects from that described in the '560 patent. It is PGN7101, shown in FIG. 4. The LtB gene of an *E. coli* strain of human origin (Leong et al.(1985) Nucleotide sequence comparison between heat-labile toxin B-subunit cistrons from *Escherichia coli* of human and porcine origin *Infect Immun*. April; 48(1):73-7) is synthesized to optimize codon usage for maize, see FIG. 5A (SEQ ID NO: 3). Oligonucleotides spanning the gene are annealed and ligated, and the products are amplified using the polymerase chain reaction (PCR). An oligonucleotide sequence encoding the barley α-amylase secretion signal (BAASS) is added at the N-terminus of LtB using PCR and this complete BAASS:LtB sequence fragment is inserted into a vector backbone resulting in the plasmid PGN543 1. The BAASS:LtB sequence is shown in FIG. 5B (SEQ ID NO: 4). The BAASS:LtB sequence is removed from PGN5431 using the restriction enzymes NcoI and HpaI and ligated into the corresponding restriction sites in the vector PGN2774 resulting the intermediate vector PGN7020. In this intermediate vector, the BAASS:LtB is placed 3' to a maize constitutive promoter and untranslated leader sequence from the ubiquitin regulatory system, designated PGNpr1 (wild type maize polyubiquitin-1), and 5' to the potato proteinase inhibitor II transcription terminator (PinII). The BAASS:LtB expression cassette (promoter, leader, BAASS:LtB and Pin II sequences) is removed from PGN7020 using the restriction enzymes NheI and NotI and ligated into the corresponding sites in the plant transformation vector PGN3770. The final BAASS:LtB transformation vector, designated PGN7101, contains the right and left border sequences of *Agrobacterium tumefaciens* Ti plasmid origin, and the pat gene of *Streptomyces viridichromogenes*, conferring resistance to glufosinate ammonium.

EXAMPLE 3

Transformation of IPNV into Plants and Detection of Expression

Infectious pancreatic necrosis virus (IPNV) infects mollusks, crustaceans and many types of fish, especially salmonids. IPNV infection can have devastating effects on salmonid production due to fish mortality at the fry or smolt stage and decreased growth in surviving populations. There have been many attempts to produce an effective vaccine against this virus. So far protection has been seen only with an injected inactivated virus, however this vaccine has proven to be expensive and impractical. The major structural and immunogenic proteins of the virus, VP2 and VP3, are expressed in maize using the methods described, supra.

Nucleotide sequences for VP2 and VP3 are initially obtained from the plasmids pUK-NVP2 and pUK-NVP3 respectively. The sequences for the proteins in these two plasmids are from a Norwegian IPNV strain closely related to the NI strain. Some nucleotide modification is carried out on the 5' and 3' ends of the gene sequences to optimize codon usage for maize.

An oligonucleotide sequence encoding 5' VP2 sequences, that are missing from the VP2 gene in pUK-NVP2, along with nucleotide changes for codon optimization, is annealed at the 5' end of the VP2 sequence from pUK-NVP2 using polymerase chain reaction (PCR). An oligonucleotide sequence encoding nucleotide changes for codon optimization at the 3' end of VP2 along with sequences from the potato proteinase inhibitor II transcription terminator (PinII) (An et al., *Plant Cell* (1989) 1:115-122) is added at the 3' end of the VP2 sequence from pUK-NVP2 using PCR. These two PCR fragments along with an internal VP2 fragment, isolated using the restriction enzymes SacII and BbsI, from pUK-NVP2 are ligated together to give the plasmid PGNK5676 containing the complete VP2 nucleotide sequence (SEQ ID NO: 5) shown in FIG. 6. An oligonucleotide sequence encoding the barley α-amylase secretion signal (BAASS) is added at the N-terminus of the restored VP2 gene using PCR. The fragment generated from PCR is put into a vector backbone resulting in the plasmid PGNK5443 containing the BAASS:VP2 nucleotide sequence (SEQ ID NO: 6) shown in FIG. 7.

Oligonucleotides encoding nucleotide changes for codon optimization for maize are annealed to both the 5' and 3' ends of the VP3 sequences, from pUK-NVP3, using PCR. The PCR fragment is put into a vector backbone to give the plasmid PGNK5581 containing the partially optimized VP3 sequence (SEQ ID NO: 7) shown in FIG. 8. An oligonucleotide sequence encoding BAASS is added to the N-terminus of VP3 using PCR. The PCR fragment is put into a vector backbone to give the plasmid PGNK5330 containing the BAASS:VP3 sequence (SEQ ID NO: 8) shown in FIG. 9.

Figure 10:
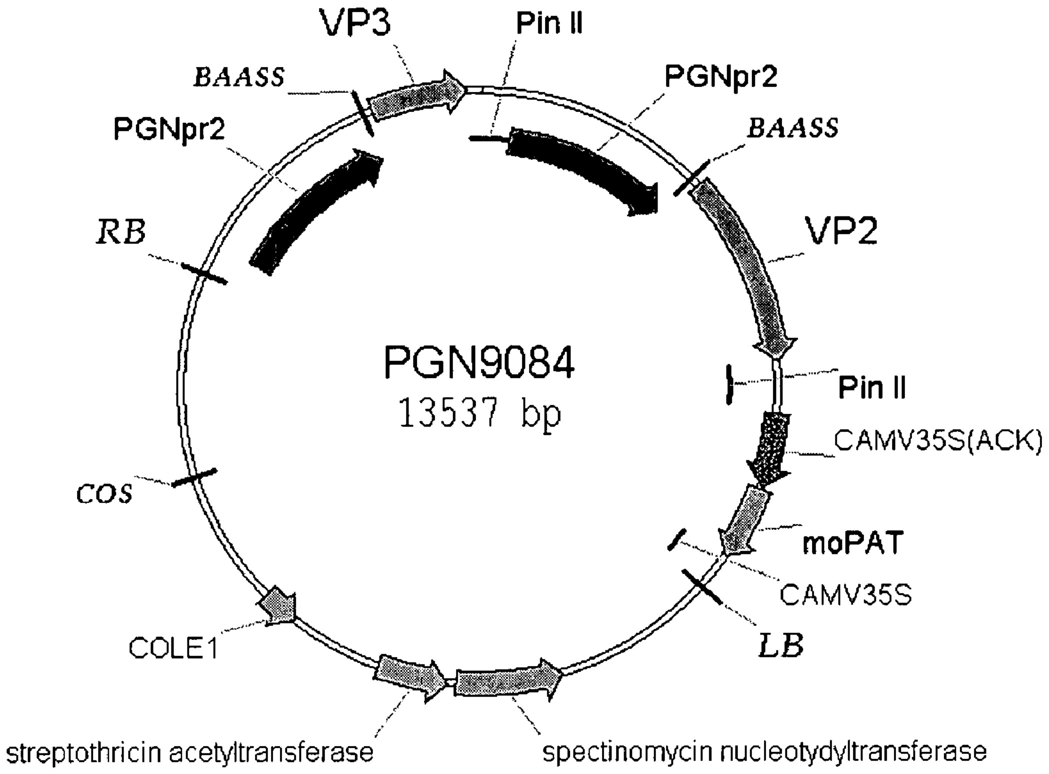
FIG. 10 is the plasmid map of PGN9084.

Two separate plant transformation vectors are constructed, each containing both of the genes for VP2 and VP3. The first construct contains the sequences for BAASS:VP2 and BAASS:VP3, each in a separate expression cassette containing a maize seed preferred promoter, designated PGNpr2, and the PinII terminator. The BAASS:VP2 sequences are cut from PGNK5443 with the restriction enzymes NcoI and PacI. This fragment along with the PGNpr2 fragment cut with the restriction enzymes HindIII and NcoI are ligated into the HindIII and PacI restriction sites of the PGN9004 plant transformation vector which contains the PinII terminator, the right and left border sequences of *Agrobacterium tumefaciens* Ti plasmid origin, and the pat gene of *Streptomyces viridichromogenes*, conferring resistance to glufosinate ammonium. This plasmid is designated PGNK5461. In a similar process the BAASS:VP3 sequences are cut from PGNK5330 using NcoI and PacI. This fragment along with the HindIII/NcoI PGNpr2 fragment is ligated into the HindIII and PacI sites of PGN9004 resulting in the plasmid PGNK5335. The BAASS:VP2 expression cassette, containing the PGNpr2 promoter, BAASS, VP2 and the PinII terminator, is cut from PGNK5461 using the restriction enzymes AscI and PacI. The BAASS:VP3 expression cassette, containing the PGNpr2 promoter, BAASS, VP3 and the PinII terminator, is cut from PGNK5335 using the restriction enzymes HindIII and MluI. These two fragments are ligated into the HindIII and PacI restriction sites of PGN9004 resulting in the final plant transformation vector containing both the BAASS:VP2 and BAASS:VP3 expression cassettes. This construct, designated PGN9084 (FIG. 10), is designed such that the proteins are sent to the cell wall and accumulate primarily in the seed. The plants are then transformed according to the modified Ishia protocol, set forth supra. Plants resulting from the transformation of PGN9084 are designated NVA.

Figure 11:
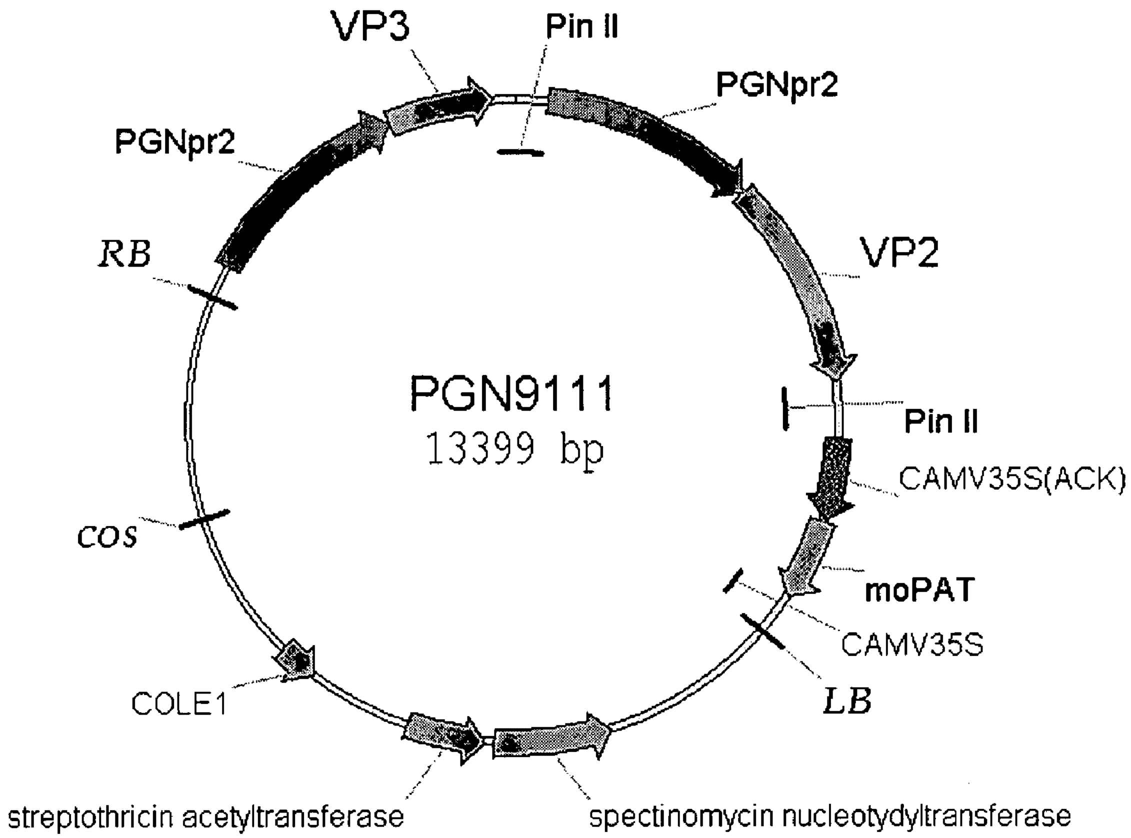
FIG. 11 is the plasmid map of PGN9111.

The second plant transformation vector also contains both VP2 and VP3 in separate expression cassettes under the control of the PGNpr2 promoter and the PinII terminator, however the barley α-amylase secretion signal (BAASS) is not present. A 5' portion of the VP2 sequence up to and including the BstBI restriction site is cut from PGNK5573 using the restriction enzymes BbsI and BstBI. This fragment and the HindIII/NcoI PGNpr2 fragment are ligated into the HindIII and BstBI sites in PGNK5461 resulting in the plasmid PGNK5676 containing the VP2 expression cassette. The VP3 sequence is cut from PGNK5581 using the restriction enzymes NcoI and PacI. This fragment and the HindIII/NcoI PGNpr2 fragment are ligated into the HindIII and PacI sites of PGN9004 resulting in the plasmid PGNK5681 containing the VP3 expression cassette. The VP2 expression cassette is cut from PGNK5676 using the restriction enzymes AscI and PacI. The VP3 expression cassette is cut from PGNK5681 using the enzymes HindIII and MluI. These two fragments are ligated into the HindIII and PacI restriction sites of PGN9004 resulting in the final plant transformation vector containing both the VP2 and VP3 expression cassettes. This construct, designated PGN9111 (FIG. 11), is designed such that the proteins are sent to the cytoplasm and accumulate primarily in the seed. Plants resulting from the transformation of PGN9111 are designated NVB.

Figure 12:
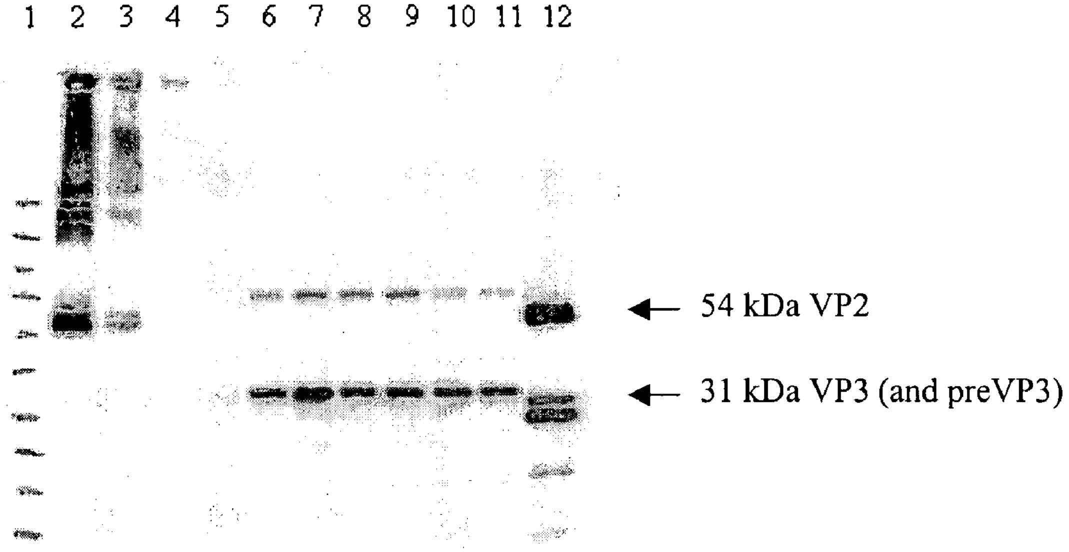
FIG. 12 is a Western blot of the VP2 and VP3 proteins expressed in seed, resulting from event NVA.

Western blot analysis using polyclonal anti-IPNV whole virus antibodies shows expression of the proteins VP2 and VP3 in both NVA and NVB seed. The VP2 and VP3 proteins expressed in NVA seed run slightly larger than the corresponding native proteins found in the IPNV whole virus standard on a Western blot (FIG. 12). Lane 1 shows protein markers, lanes 2-4 a purified prep of IPNV whole virus, lane 5 control maize seed extract, negative control, lanes 6-11 extracts from various NVA seed and lane 12 an unpurified prep of IPNV whole virus. (Note, the purification process of the whole virus generates the smearing pattern in the top of those wells).

Figure 13:
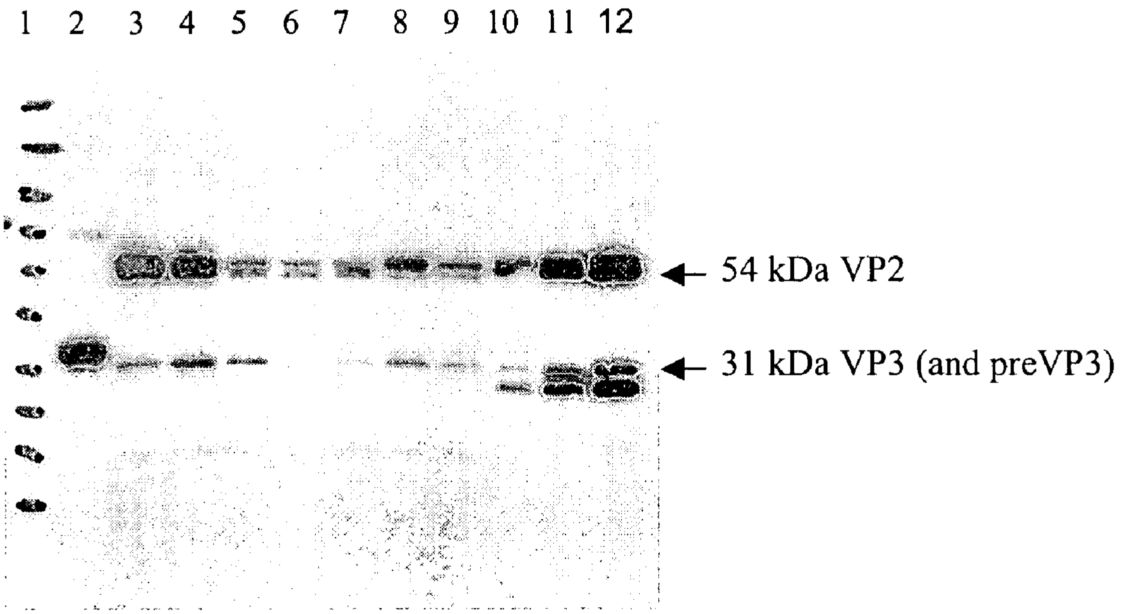
FIG. 13 is a Western blot of the VP2 and VP3 proteins expressed in seed, resulting from event NVB.

Since the VP2 and VP3 proteins are targeted by the BAASS to the cell wall in the NVA seed, it is expected that the proteins will be glycosylated. Not wishing to be bound by theory, it is possible that this increase in size of both proteins suggests glycosylation of the proteins in the plant. Both VP2 and VP3 expressed in NVB seed run at the expected sizes compared to the IPNV whole virus standard on a Western blot (FIG. 13). Lane 1 shows protein markers, lane 2 extract from NVA seed, lanes 3-9 extracts from various NVB seed, and lanes 10-12 increasing amounts of unpurified IPNV whole virus.

Since these proteins are expressed in the cytoplasm of the plant cell, no modification of the proteins is expected.

Expression levels of VP2 and VP3 in the NVA seed are measured by means of a Western blot. The intensity of the VP2 and VP3 protein bands from the seed extracts are measured using spot densitometry and are then compared to the bands of known amounts of whole virus. Using this method the expression of VP2 in NVA T2 seed is calculated to be 0.1% TSP (total soluble protein) and the expression of VP3 in NVA T2 seed is calculated to be 0.3% TSP. Expression levels of VP2 in the NVB seed are measured by ELISA. The ELISA is a typical sandwich style in which the microtiter plate is coated with sheep anti-IPNV whole virus antiserum, the IPNV protein in the plant extract is captured overnight at 4° C., and the plate is reacted with AS1 mouse monoclonal anti-VP2 antibody followed by alkaline phosphatase conjugated sheep anti-mouse IgG. The alkaline phosphatase is detected with para-nitrophenyl phosphate, disodium (pNpp) and read at 405 nm on an absorbance microplate reader. Using his method the expression of VP2 in NVB T1 seed is measured to be 0.17% TSP in the highest single seeds.

EXAMPLE 4

Feeding Studies with Avidin and LtB

To evaluate this new technology in fish, this experiment is designed to determine if oral administration of diets containing corn-expressed recombinant marker proteins induces a humoral immune response in salmonids. Atlantic salmon are fed, in an amount of approximately 2% of body weight per day, diets containing two doses of unpurified corn expressing LtB (5% or 10% of food) or chicken egg white avidin (10% or 20% of food) for 5 days, 12 days with normal food and 5 days with the treated diet. Groups of fish are also intraperitoneally injected with purified LtB and avidin protein as positive controls.

Fish growth, persistence of recombinant proteins in feces and humoral immune response are examined. Fish antibody response is compared for the different doses of LtB, which has been shown previously to be capable of producing a strong antibody response in mice, and avidin, which has been shown previously to be a weaker antigen in mice.

The Atlantic salmon weigh about 20 grams each. There are a total of eleven treatment groups with several negative and positive control groups (Table 1). A and B positive control groups, each consisting of ten fish, are given an intraperitoneal injection with oil-adjuvanted preparations with group A receiving a single injection of 4 μg LtB protein per fish and group B receiving a single injection of 20 μg avidin protein per fish which are both recombinant proteins purified from a corn expression system. Nine groups each contain 35 fish, with group C to G being negative controls. Group C receives commercial fish pellets. Group D receives pellets which include 5% non-transgenic corn germ. Group E receives pellets with 10% non-transgenic corn germ. Group F receives pellets made with fish meal having 10% non-transgenic corn flour and Group G receives pellets with 20% non-transgenic corn flour. In the experimental groups, Group H receives fish pellets with 5% LtB transgenic corn germ, and group I receives pellets with 10% LtB corn germ. Group J receives pellets with 10% transgenic avidin-containing flour, and group K receives pellets with 20% avidin flour.

TABLE 1

| Group | Vaccine | Number of Fish | Weight (g) corn required | Total protein amount (mg) | Feed (g) for 10 days |
|---|---|---|---|---|---|
| A | Injected Lt-B positive control | 10 | 0 | 0.040* | 40 |
| B | Injected Avidin positive control | 10 | 0 | 0.20* | 40 |
| C | Negative Control 1 (normal food) | 35 | 0 | 0 | 140 |
| D | Negative Control 2 5% normal corn germ meal | 35 | 0 | 0 | 140 |
| E | Negative Control 2 10% normal corn germ meal | 35 | 0 | 0 | 140 |
| F | Negative Control 4 10% normal corn flour | 35 | 14 | 0 | 140 |
| G | Negative Control 5 20% normal corn flour | 35 | 28 | 0 | 140 |
| H | 5% recombinant LtB corn germ meal | 35 | 7 | 2.1 | 140 |
| I | 10% recombinant LtB corn germ meal | 35 | 14 | 4.2 | 140 |
| J | 10% avidin corn flour | 35 | 14 | 20.61 | 140 |
| K | 20% avidin corn flour | 35 | 28 | 41.22 | 140 |

*Each fish is given an intraperitoneal (ip) injection of 0.1 ml PBS containing 40 μg purified recombinant Lt-B (group A), or 200 μg avidin (group B) in an oil adjuvant.

Fish are maintained at 10° C. At two, four, seven, fourteen and twenty one days post-feeding five fish are sacrificed in nine diet groups C-K to measure the persistence of the recombinant proteins in the feces using an ELISA. At eight weeks, ten fish in all eleven groups are sacrificed weighed and specific antibody in the serum is measured by ELISA ELISA to Detect Marker Proteins in Feces:

ELISA is the typical sandwich style in which the microtiter plates are coated overnight at 4° C. with rabbit anti-avidin or anti-LtB antibody. Fish fecal samples, diluted in PBST, are added to wells and the plate incubated overnight at 4° C. to allow capture of the avidin or LtB protein. The plate is reacted with goat anti-avidin antibody (Vector Labs, Burlingame, Calif.) or mouse biotinylated LtB antibody followed by anti-goat alkaline phosphatase conjugate (Jackson Immunoresearch, West Grove, Pa.) or ExtraAvidin-alkaline phosphatase (Sigma-Aldrich Canada Ltd., Oakdale, ON). The alkaline phosphatase is detected with para-nitrophenyl phosphate (Pierce, distributor MJS Biolynx Inc., Brockville, ON, Canada) and read at 405 nm on a plate reader (BioTek Instruments Inc., Vermont).

ELISA to Detect Specific Anti-Avidin and Anti-LtB Antibodies in Fish Serum:

A sandwich ELISA is used to detect specific antibodies in fish serum. Plate wells are coated with purified LtB or purified corn-expressed avidin (Sigma) overnight at 4° C., two-fold dilutions of fish serum in PBST-1% BSA are added and the plates incubated overnight at 17° C. to allow fish antibody capture. Primary antibody, monoclonal anti-Atlantic salmon Ig (Cedarlane Laboratories Ltd., ON, Canada), followed by secondary alkaline-phosphatase labeled anti-mouse Ig antibody (Cedarlane), both diluted in PBST-1% BSA, are added to the plates. After the addition of para-nitrophenyl phosphate substrate (Pierce), absorbance is read at 405 nm using a microtiter plate reader (BioTek Instruments). Antibody titer is calculated as the endpoint dilution.

Figure 14:
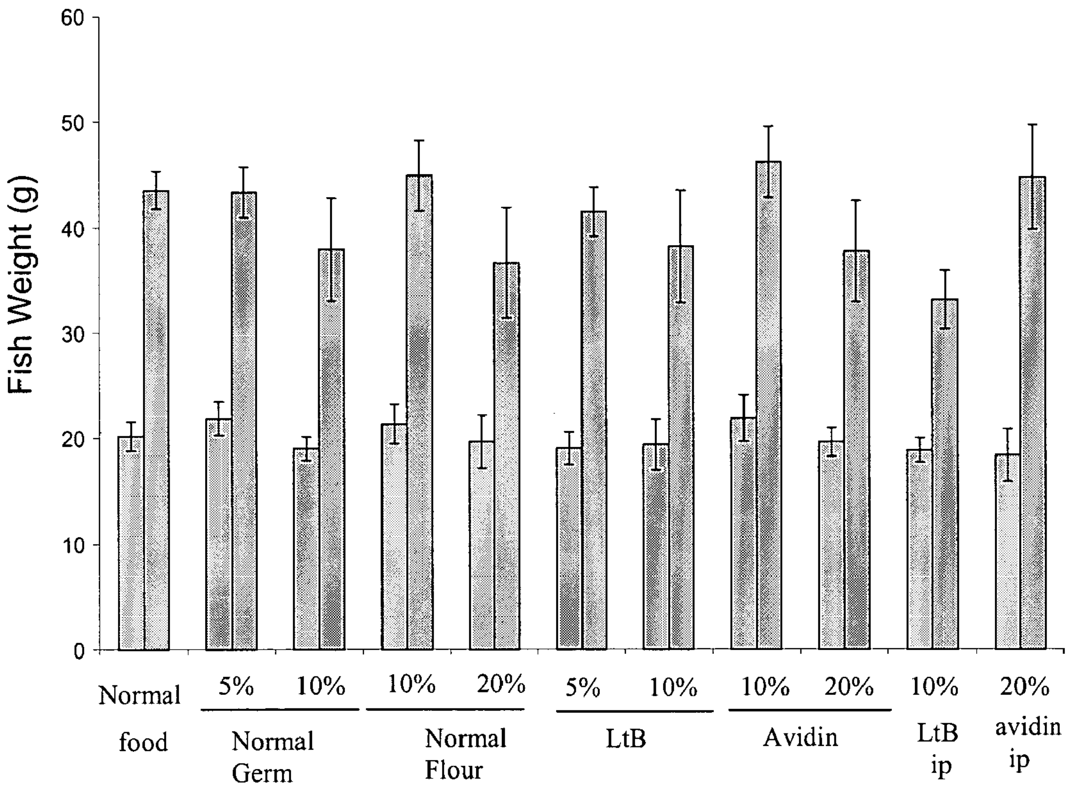
FIG. 14 is a graph showing mean weight of fish at the time 0 (first bar) and 8 weeks after vaccination (second bar). Standard error bars are also shown FIG. 15 are graphs showing mean antibody response of Atlantic salmon at 8 weeks post-injection or feeding of recombinant avidin (A) or LtB (B) expressed in corn as measured by ELISA. Bars represent the standard error of the mean. The number of animals sampled in each group (N) is indicated for each group.

The addition of ground corn expressing the two marker proteins to the diet does not affect fish growth as shown in FIG. 14. The two marker proteins are detectable for an extended time period in the feces, at least 21 days after cessation of feeding the treated diet as shown in Table 2.

TABLE 2

| | Day Post-Feeding | | | | |
|---|---|---|---|---|---|
| Group | 2 | 4 | 7 | 14 | 21 |
| 5% LtB | 5/5 | 4/4 | 5/5 | 4/5 | NS |
| 10% LtB | 5/5 | 4/4 | 3/4 | 3/4 | 2/4 |

TABLE 2-continued

| Group | Day Post-Feeding 2 | 4 | 7 | 14 | 21 |
|---|---|---|---|---|---|
| 10% avidin | 5/5 | 5/5 | 4/5 | 5/5 | 4/4 |
| 20% avidin | 3/3 | 4/4 | 5/5 | 4/4 | 4/4 |

Figure 15:
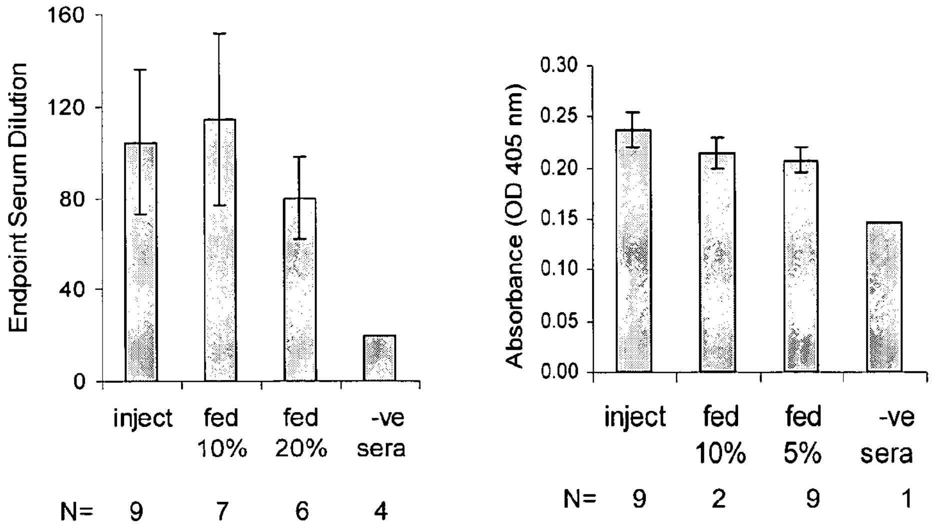

Oral administration of the marker proteins induces a humoral immune response. At 8 weeks post-vaccination, only fish in the negative control groups do not have a detectable specific serum antibody response. The antibody response of fish fed unpurified corn-expressed marker proteins is as strong as those of fish injected with pure proteins in oil adjuvant as shown in FIG. 15.

EXAMPLE 5

Feeding Studies with IPNV

The methods described in feeding the corn containing infectious pancreatic necrosis virus VP2 and VP3 proteins will be completed. The presence of the viral proteins in the feces and organs of the animal is expected, as well as antibody responses After fish are challenged with virulent virus it is expected that oral administration of the corn-expressed IPNV proteins will result in protection.

Fish will be divided into seven groups and tagged for identification. Positive control group A will consist of fish given an injection with a commercial vaccine that induces protection against IPNV and negative control group B will be fed commercial food pellets. The remaining groups will be fed food containing corn germ with and without expressed IPNV proteins for 5 days, 12 days with normal food and 5 days with food containing corn germ as outlined in Table 3. The percent incorporation rate of corn germ into food (g corn per g food) will be 10% and 20%.

TABLE 3

| Group | Number of fish | Treatment |
|---|---|---|
| A | 55 | ip injected commercial vaccine |
| B | 55 | normal food |
| C | 85 | non-transgenic corn germ mixed into food 20% incorporation |
| D | 85 | NVA corn germ 10% incorporation |
| E | 85 | NVA corn germ 20% incorporation |
| F | 85 | NVB corn germ 10% incorporation |
| G | 85 | NVB corn germ 20% incorporation |

At 4 weeks post-vaccination, all fish will acclimated over a few days to salt water and then maintained in flowing salt water at ambient temperature (9-12° C.).

At 5 weeks post-transfer to salt water, fish will be exposed to a cohabitation IPNV challenge. Naive fish will be injected with live IPNV and added to tanks containing the vaccinated fish. Daily mortality will be monitored for five weeks.

On a weekly basis from 1 to 5 weeks post-vaccination and at the time of challenge, 5 fish per groups C to G will be sacrificed and sampled for feces and organs to examine IPNV protein persistence and distribution. Fish killed at the time of challenge, including 5 fish in groups A and B, will also be bled and the serum tested for antibodies by ELISA.

What is claimed is:

1. A plant comprising a recombinant nucleotide sequence integrated into the plant genome, the sequence encoding an amino acid sequence which, when orally administered to a fish, results in a protective response in said fish, wherein the nucleotide sequence comprises SEQ ID NO: 5.

2. A composition for administration to a fish, comprising plant material comprising a recombinant nucleotide sequence integrated into the genome of the plant material, the sequence encoding an amino acid sequence that is an antigen of an organism that causes disease or pathology in fish, which, when administered to a fish, results in a protective response in said fish, wherein the nucleotide sequence comprises SEQ ID NO: 5.

* * * * *

SEQUENCE LISTING

```
<160> NUMBER OF SEQ ID NOS: 8

<210> SEQ ID NO 1
<211> LENGTH: 459
<212> TYPE: DNA
<213> ORGANISM: Hordeum vulgare

<400> SEQUENCE: 1

atggccaaca agcacctgag cctctccctc ttcctcgtgc tcctcggcct ctccgcctcc     60

ctcgccagcg gcgccaggaa gtgctccctc accggcaagt ggaccaatga cctcggctcc    120

aacatgacca tcggcgccgt gaactccagg ggcgagttca ccggcaccta catcaccgcc    180

gtgaccgcca cctccaacga gatcaaggag tcccccctcc acggtaccca gaacaccatc    240

aacaagagga cccagcccac cttcggcttc accgtgaact ggaagttctc cgagtccacc    300

accgtgttca ccggccagtg cttcatcgac cgcaacggca aggaggtgct caagaccatg    360

tggctcctga ggagctccgt gaatgacatc ggcgacgact ggaaggccac ccgcgtgggc    420

atcaacatct tcacccgcct ccgcacccag aaggagtga                           459


<210> SEQ ID NO 2
<211> LENGTH: 552
<212> TYPE: DNA
<213> ORGANISM: Zea mays

<400> SEQUENCE: 2
```

-continued

```
atgtcccccg agcgccgccc cgtcgagatc cgcccggcca ccgccgccga catggccgcc      60

gtgtgcgaca tcgtgaacca ctacatcgag acctccaccg tgaacttccg caccgagccg     120

cagaccccgc aggagtggat cgacgacctg gagcgcctcc aggaccgcta cccgtggctc     180

gtggccgagg tggagggcgt ggtggccggc atcgcctacg ccggcccgtg gaaggcccgc     240

aacgcctacg actggaccgt ggagtccacc gtgtacgtgt cccaccgcca ccagcgcctc     300

ggcctcggct ccaccctcta cacccacctc ctcaagagca tggaggccca gggcttcaag     360

tccgtggtgg ccgtgatcgg cctcccgaac gacccgtccg tgcgcctcca cgaggccctc     420

ggctacaccg cccgcggcac cctccgcgcc gccggctaca agcacggcgg ctggcacgac     480

gtcggcttct ggcagcgcga cttcgagctg ccggccccgc cgcgcccggt gcgcccggtg     540

acgcagatct ga                                                         552
```

<210> SEQ ID NO 3
<211> LENGTH: 309
<212> TYPE: DNA
<213> ORGANISM: Zea mays

<400> SEQUENCE: 3

```
gccccgcagt ccatcaccga gctctgctcc gagtaccaca acacccagat ctacaccatc      60

aacgacaaga tcctctccta caccgagagc atggccggca agcgcgagat ggtgatcatc     120

accttcaagt ccggcgccac cttccaggtg gaggtgccgg gctcccagca catcgactcc     180

cagaagaagg ccatcgagcg catgaaggac accctccgca tcacctacct caccgagacc     240

aagatcgaca agctctgcgt gtggaacaac aagaccccga actccatcgc cgccatcagc     300

atggagaac                                                             309
```

<210> SEQ ID NO 4
<211> LENGTH: 382
<212> TYPE: DNA
<213> ORGANISM: Hordeum vulgare

<400> SEQUENCE: 4

```
atggccaaca agcacctgag cctctccctc ttcctcgtgc tcctcggcct ctccgcctcc      60

ctcgccagcg gcgccccgca gtccatcacc gagctctgct ccgagtacca caacacccag     120

atctacacca tcaacgacaa gatcctctcc tacaccgaga gcatggccgg caagcgcgag     180

atggtgatca tcaccttcaa gtccggcgcc accttccagg tggaggtgcc gggctcccag     240

cacatcgact cccagaagaa ggccatcgag cgcatgaagg acaccctccg catcacctac     300

ctcaccgaga ccaagatcga caagctctgc gtgtggaaca acaagacccc gaactccatc     360

gccgccatca gcatggagaa ct                                              382
```

<210> SEQ ID NO 5
<211> LENGTH: 1413
<212> TYPE: DNA
<213> ORGANISM: Infectious pancreatic necrosis virus

<400> SEQUENCE: 5

```
aacaccaaca aggcaaccgc aacttacttg aaatccatca tgcttccaga gactggacca      60

gcaagcatcc cggacgacat aacggagaga cacatcctaa aacaagagac ctcgtcatac     120

aacctagagg tctccgaatc aggaagtggc attcttgttt gtttccctgg ggcaccaggc     180

tcacggatcg gtgcacacta cagatggaat gcgaaccaga cggggctgga gttcgaccag     240

tggctggaga cgtcgcagga cctgaagaaa gccttcaact acgggaggct gatctcaagg     300
```

-continued

```
aaatacgaca tccaaagctc cacactaccg gccggtctct atgctctgaa cgggacgctc    360
aacgctgcca ccttcgaagg cagtctgtct gaggtggaga gcctgaccta caacagcctg    420
atgtccctaa caacgaaccc ccaggacaaa gtcaacaacc agctggtgac caaaggagtc    480
acagtcctga atctaccaac agggttcgac aaaccatacg tccgcctaga ggacgagaca    540
ccccagggtc tccagtcaat gaacggggcc aagatgaggt gcacagctgc aattgcaccg    600
cggaggtacg agatcgacct cccatcccaa cgcctacccc ccgttcctgc gacaggaacc    660
ctcaccactc tctacgaggg aaacgccgac atcgtcaact ccacaacagt gacgggagac    720
ataaacttca gtctggcaga acaacccgca aacgagacca agttcgactt ccagctggac    780
ttcatgggcc ttgacaacga cgtcccagtt gtcacagtgg tcagctccgt gctggccaca    840
aatgacaact acagaggagt ctcagccaag atgacccagt ccatcccgac cgagaacatc    900
acaaagccga tcaccagggt caagctgtca tacaagatca accagcagac agcaatcggc    960
aacgtcgcca ccctgggcac aatgggtcca gcatccgtct ccttctcatc agggaacgga   1020
aatgtccccg gcgtgctcag accaatcaca ctggtggcct atgagaagat gacaccgctg   1080
tccatcctga ccgtagctgg agtgtccaac tacgagctga tcccaaaccc agaactcctc   1140
aagaacatgg tgacacgcta tggcaagtac gaccccgaag gtctcaacta tgccaagatg   1200
atcctgtccc acagggaaga gctggacatc aggacagtgt ggaggacaga ggagtacaag   1260
gagaggacca gagtcttcaa cgaaatcacg gacttctcca gtgacctgcc cacgtcaaag   1320
gcatggggct ggagagacat agtcagagga attcggaaag tcgcagctcc tgtactgtcc   1380
acgctgtttc caatggcagc accactcatc gga                                1413
```

<210> SEQ ID NO 6
<211> LENGTH: 1485
<212> TYPE: DNA
<213> ORGANISM: Hordeum vulgare

<400> SEQUENCE: 6

```
atggcgaaca agcacctgag ccttagcctc ttcctcgtgc tcctgggcct ctccgcctcc     60
ctcgcctccg gcaacaccaa caaggcaacc gcaacttact tgaaatccat catgcttcca    120
gagactggac cagcaagcat cccggacgac ataacggaga gacacatcct aaaacaagag    180
acctcgtcat acaacctaga ggtctccgaa tcaggaagtg gcattcttgt ttgtttccct    240
ggggcaccag gctcacggat cggtgcacac tacagatgga atgcgaacca gacggggctg    300
gagttcgacc agtggctgga gacgtcgcag gacctgaaga aagccttcaa ctacgggagg    360
ctgatctcaa ggaaatacga catccaaagc tccacactac cggccggtct ctatgctctg    420
aacgggacgc tcaacgctgc caccttcgaa ggcagtctgt ctgaggtgga gagcctgacc    480
tacaacagcc tgatgtccct aacaacgaac ccccaggaca aagtcaacaa ccagctggtg    540
accaaaggag tcacagtcct gaatctacca acagggttcg acaaaccata cgtccgccta    600
gaggacgaga caccccaggg tctccagtca atgaacgggg ccaagatgag gtgcacagct    660
gcaattgcac cgcggaggta cgagatcgac ctcccatccc aacgcctacc ccccgttcct    720
gcgacaggaa ccctcaccac tctctacgag ggaaacgccg acatcgtcaa ctccacaaca    780
gtgacgggag acataaactt cagtctggca gaacaacccg caaacgagac caagttcgac    840
ttccagctgg acttcatggg ccttgacaac gacgtcccag ttgtcacagt ggtcagctcc    900
gtgctggcca caaatgacaa ctacagagga gtctcagcca agatgaccca gtccatcccg    960
```

-continued

```
accgagaaca tcacaaagcc gatcaccagg gtcaagctgt catacaagat caaccagcag   1020

acagcaatcg gcaacgtcgc caccctgggc acaatgggtc cagcatccgt ctccttctca   1080

tcagggaacg gaaatgtccc cggcgtgctc agaccaatca cactggtggc ctatgagaag   1140

atgacaccgc tgtccatcct gaccgtagct ggagtgtcca actacgagct gatcccaaac   1200

ccagaactcc tcaagaacat ggtgacacgc tatggcaagt acgaccccga aggtctcaac   1260

tatgccaaga tgatcctgtc ccacagggaa gagctggaca tcaggacagt gtggaggaca   1320

gaggagtaca aggagaggac cagagtcttc aacgaaatca cggacttctc cagtgacctg   1380

cccacgtcaa aggcatgggg ctggagagac atagtcagag gaattcggaa agtcgcagct   1440

cctgtactgt ccacgctgtt tccaatggca gcaccactca tcgga                   1485
```

<210> SEQ ID NO 7
<211> LENGTH: 705
<212> TYPE: DNA
<213> ORGANISM: Infectious pancreatic necrosis virus

<400> SEQUENCE: 7

```
gacgaggagc tgcagcgcct cctgaacgcc acgatggcca gggccaagga ggtccaggac     60

gccgagatct acaaacttct taagctcatg gcatggacca gaaagaacga cctcaccgac    120

cacatgtacg agtggtcaaa agaggacccc gatgcactaa agttcggaaa gctcatcagc    180

acgccaccaa agcaccctga gaagcccaaa ggaccagacc aacaccacgc ccaagaggcg    240

agagccaccc gcatatcatt ggacgccgtg agagccgggg cggacttcgc cacaccggaa    300

tgggtcgcgc tgaacaacta ccgcggccca tctcccgggc agttcaagta ctacctgatc    360

actggacgag aaccagaacc aggcgacgag tacgaggact acataaaaca acccattgtg    420

aaaccgaccg acatgaacaa aatcagacgt ctagccaaca gtgtgtacgg cctcccacac    480

caggaaccag caccagagga gttctacgat gcagttgcag ctgtattcgc acagaacgga    540

ggcagaggtc ccgaccagga ccaaatgcaa gacctcaggg agctcgcaag acagatgaaa    600

cgcaggccca ggaacgccga tgcgccacgc aggaccaggg cgccagcgga accggcaccg    660

cccggacgct caaggttcac gcccagcgga gacaacgctg aggtg                    705
```

<210> SEQ ID NO 8
<211> LENGTH: 777
<212> TYPE: DNA
<213> ORGANISM: Hordeum vulgare

<400> SEQUENCE: 8

```
atggcgaaca agcacctgag ccttagcctc ttcctcgtgc tcctgggcct ctccgcctcc     60

ctcgcctccg gcgacgagga gctgcagcgc ctcctgaacg ccacgatggc cagggccaag    120

gaggtccagg acgccgagat ctacaaactt cttaagctca tggcatggac cagaaagaac    180

gacctcaccg accacatgta cgagtggtca aaagaggacc ccgatgcact aaagttcgga    240

aagctcatca gcacgccacc aaagcaccct gagaagccca aaggaccaga ccaacaccac    300

gcccaagagg cgagagccac ccgcatatca ttggacgccg tgagagccgg ggcggacttc    360

gccacaccgg aatgggtcgc gctgaacaac taccgcggcc catctcccgg gcagttcaag    420

tactacctga tcactggacg agaaccagaa ccaggcgacg agtacgagga ctacataaaa    480

caacccattg tgaaaccgac cgacatgaac aaaatcagac gtctagccaa cagtgtgtac    540

ggcctcccac accaggaacc agcaccagag gagttctacg atgcagttgc agctgtattc    600

gcacagaacg gaggcagagg tcccgaccag gaccaaatgc aagacctcag ggagctcgca    660
```

-continued

```
agacagatga aacgcaggcc caggaacgcc gatgcgccac gcaggaccag ggcgccagcg    720

gaaccggcac cgcccggacg ctcaaggttc acgcccagcg gagacaacgc tgaggtg       777
```